United States Patent [19]

Gentry

[11] 4,303,393
[45] Dec. 1, 1981

[54] DENTAL HANDPIECE

[76] Inventor: Don C. Gentry, 1810 SW. Blvd., Jefferson City, Mo. 65101

[21] Appl. No.: 87,414

[22] Filed: Oct. 22, 1979

Related U.S. Application Data

[63] Continuation-in-part of Ser. No. 874,381, Feb. 2, 1978, abandoned.

[51] Int. Cl.³ ............................................. A61C 1/12
[52] U.S. Cl. .................................. 433/130; 433/132; 433/133
[58] Field of Search .............. 433/130, 124, 132, 133; 415/503

[56] References Cited

U.S. PATENT DOCUMENTS

| | | | |
|---|---|---|---|
| 491,499 | 2/1893 | Sharp | 433/128 |
| 522,291 | 7/1894 | Davis | 433/130 |
| 553,124 | 1/1896 | Meister | 433/130 |
| 662,070 | 11/1900 | Jones | 433/130 |
| 1,170,524 | 2/1916 | Fernald | 433/130 |
| 1,333,809 | 3/1920 | Laurer et al. | 433/130 |
| 1,412,400 | 4/1922 | Gasser | 415/503 |
| 1,621,190 | 3/1927 | Brown | 433/133 |
| 2,453,349 | 11/1948 | Stalder | 433/130 |
| 2,813,337 | 11/1957 | Uhler | 433/133 |
| 3,092,908 | 6/1963 | Flatland | 433/132 |
| 3,164,903 | 1/1965 | Ellis | 433/124 |
| 3,727,312 | 4/1973 | Durante | 433/130 |
| 3,955,284 | 5/1976 | Balson | 433/126 |
| 4,020,556 | 5/1977 | Sotman | 433/133 |

FOREIGN PATENT DOCUMENTS

| | | | |
|---|---|---|---|
| 2334448 | 1/1975 | Fed. Rep. of Germany | 433/126 |
| 289192 | 2/1953 | Sweden | 433/130 |
| 226789 | 1/1969 | U.S.S.R. | 433/132 |

*Primary Examiner*—Gene Mancene
*Assistant Examiner*—John J. Wilson
*Attorney, Agent, or Firm*—Gravely, Lieder & Woodruff

[57] ABSTRACT

A dental handpiece includes a handle, a shank projected from the forward end of the handle, a turbine head on the forward end of the shank, and a turbine type dental engine in the head, with the engine being capable of holding and rotating a suitable dental bur. The head may be secured to the shank in a fixed position, with the engine axis at an oblique angle to the handle axis, the angle being such that regions and surfaces heretofore inaccessible to the dental bur are now easily accessible. Also the head may be coupled to the shank such that it pivots relative to the shank and handle, in which case, the axis of the dental engine and bur may be varied to suit the particular dental procedure that is to be performed. Means are provided for locking the head in the selected position.

14 Claims, 13 Drawing Figures

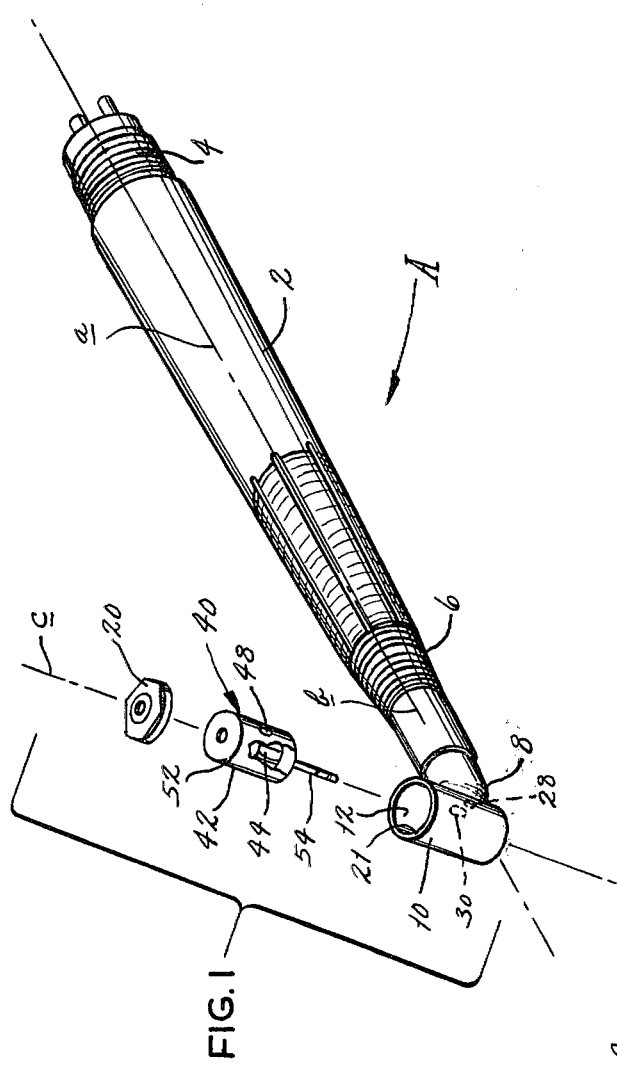
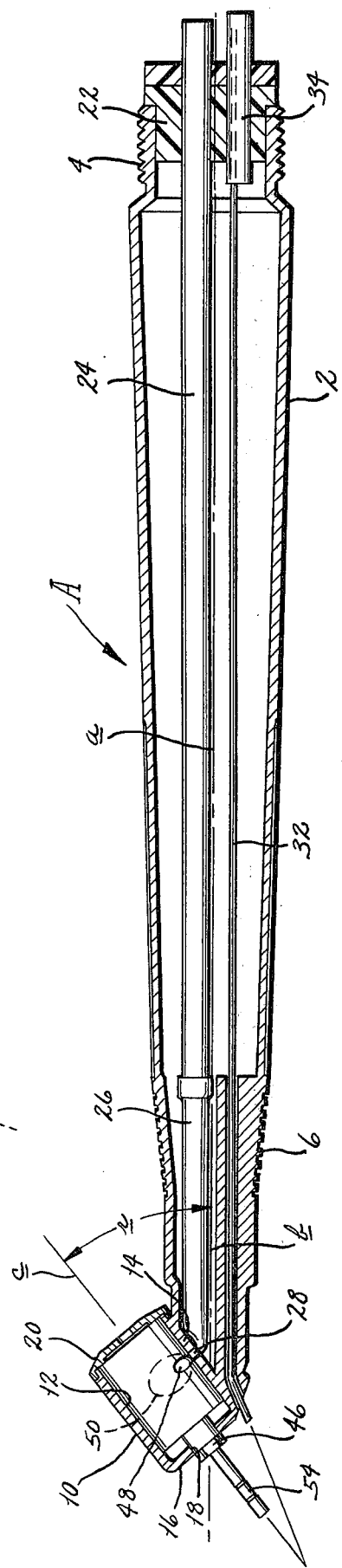
FIG. 1
FIG. 2

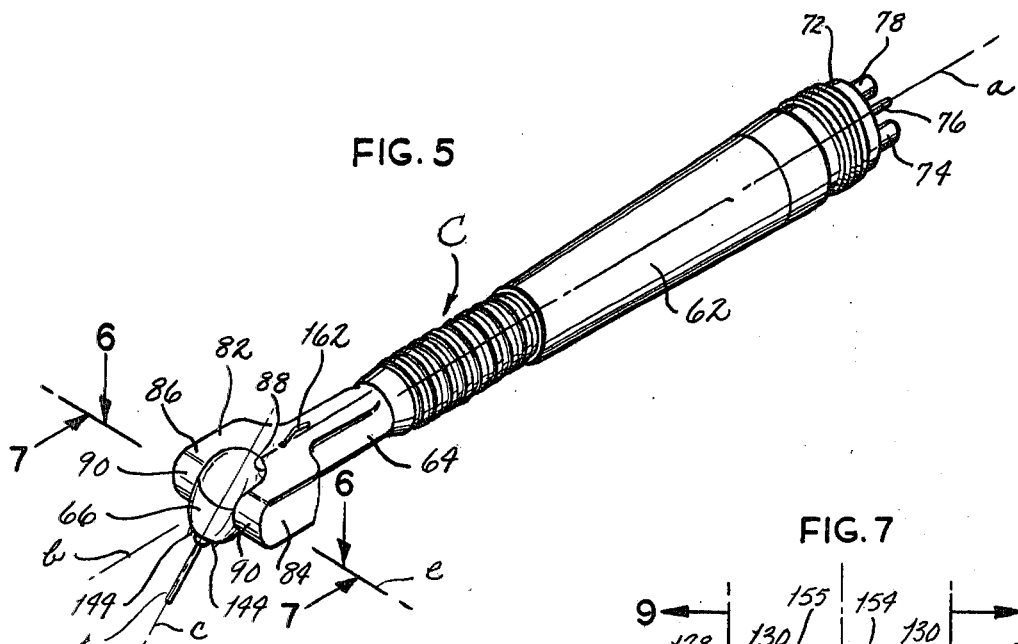
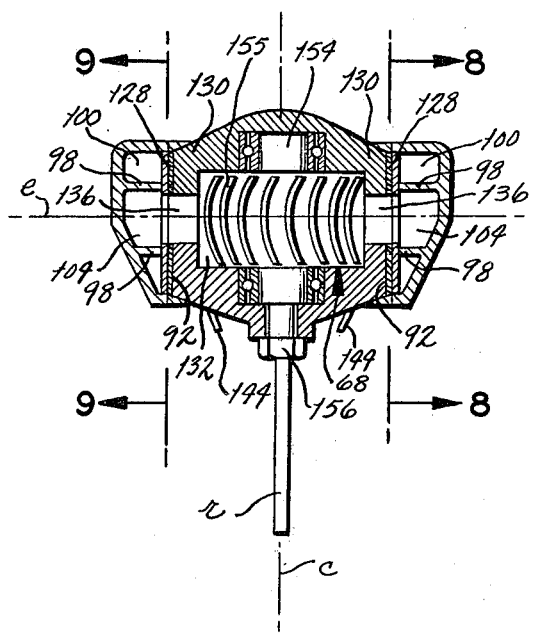
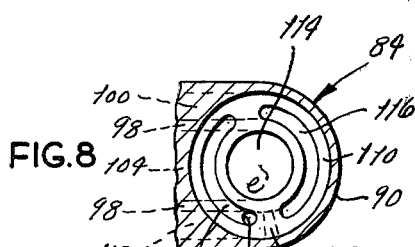
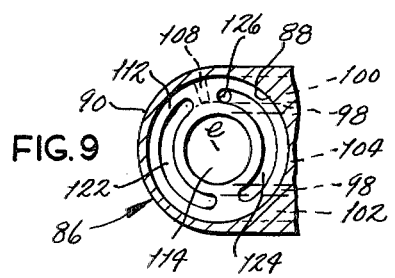
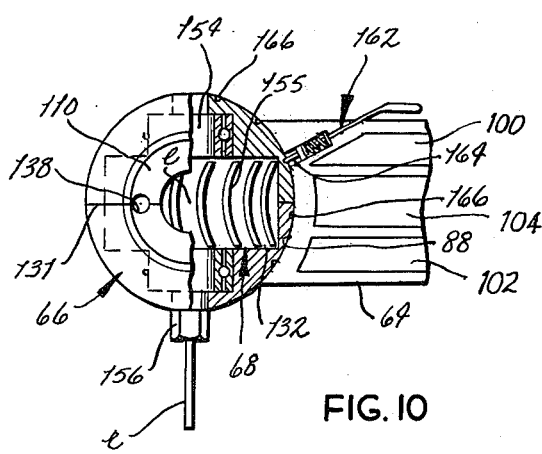

DENTAL HANDPIECE

RELATED APPLICATION

This application is a continuation-in-part of application Ser. No. 874,381, filed Feb. 2, 1978, and now abandoned, and entitled Dental Surgical Handpiece.

BACKGROUND OF THE INVENTION

This invention relates in general to dental implements, and more particularly to dental handpieces having turbine engines.

The conventional dental handpiece of current manufacture possesses a handle, a shank of somewhat smaller diameter projected from the forward end of the handle at a slight angle, and turbine engine at the forward end of the shank. The turbine engine, to which the surgical or dental bur attaches, rotates about an axis that is perpendicular to the axis of the shank. While this angle is suitable for many dental procedures, it is awkward for others, particularly those involving the second and third molars at the back of the mouth and the distal areas of other teeth. For example, in order to extract an impacted third molar, the tooth is normally cut into segments with a surgical bur and these segments removed individually from their bony sockets. However, the roots of impacted third molars are practically inaccessible to a bur that is oriented at 90° with respect to its shank, and as a consequence impacted third molars are extremely difficult to extract. Similarly distal cavities in the second and third molars are not easily prepared for filling with conventional 90° handpieces. Usually such cavities are approached from the occlusal or chewing surfaces, and this often requires the removal of a considerable amount of healthy tooth structure to reach the decayed structure. Moreover, even those dental procedures which can be effectively performed with 90° handpieces, can often be more easily performed with a handpiece having its angle tailored to the particular procedure. Indeed, for each dental procedure an optimum angle exists for the handpiece, and this angle is more often than not some angle other than 90°. Thus, the conventional 90° handpiece is not ideally suited for most dental procedures.

Aside from the foregoing, turbine-type dental engines of current manufacture have relatively low torque and therefore the handpiece must be manipulated quite adroitly to maintain the engine at an acceptable operating speed. With greater torque many procedures requiring the use of dental handpieces could be shortened considerably.

SUMMARY OF THE INVENTION

One of the principal objects of the present invention is to provide a dental handpiece of the turbine variety that is capable of reaching regions of the mouth that are practically inaccessible or at least not easily accessible with conventional turbine handpieces. Another object is to provide a handpiece that is ideally suited for impacted molars that must be removed surgically. A further object is to provide a handpiece that is ideally suited for working on the distal areas of teeth. An additional object is to provide a single handpiece which enables the user to vary the angle between the turbine and the shank on which the turbine is mounted. Still another object is to provide a handpiece that delivers significantly greater torque than conventional turbine handpieces. These and other objects and advantages will become apparent hereinafter.

The present invention is embodied in a dental handpiece having a handle, a shank extended from the handle, a turbine head on the end of the handle, and a turbine engine in the turbine head. The head in some embodiments is mounted in a fixed position on the shank such that an oblique angle exists between the axis of rotation for the engine, on one hand, and the axis of the shank as well as the axis of the handle on the other. In other embodiments, the head pivots relative to the shank so that the angle of the turbine engine may be adjusted. The invention further includes a handpiece containing a dental engine that is supplied with pressurized air at two locations around its axis of rotation. The invention also consists in the parts and in the arrangements and combinations of parts hereinafter described and claimed.

DESCRIPTION OF THE DRAWINGS

In the accompanying drawings which form part of the specification and wherein like numerals and letters refer to like parts wherever they occur:

FIG. 1 is a perspective view of a dental handpiece embodying the present invention and showing the components of the head exploded;

FIG. 2 is a side view, partially cut away and in section, of the handpiece;

FIG. 5 is a perspective view of another modified handpiece having a turbine head that pivots and a turbine engine into which two streams of pressurized air are directed;

FIG. 6 is a sectional view taken along line 6—6 of FIG. 5;

FIG. 7 is a sectional view taken along line 7—7 of FIG. 5;

FIG. 8 is a sectional view taken along line 8—8 of FIG. 7 and showing the arrangement of apertures and grooves in the plate that overlies the one arm of the yoke;

FIG. 9 is a sectional view taken along line 9—9 of FIG. 7 and showing the arrangement of grooves and apertures in the other arm of the yoke;

FIG. 10 is a sectional view taken along line 10—10 of FIG. 6 and showing the turbine head in side elevation.

DETAILED DESCRIPTION

Figure 3:
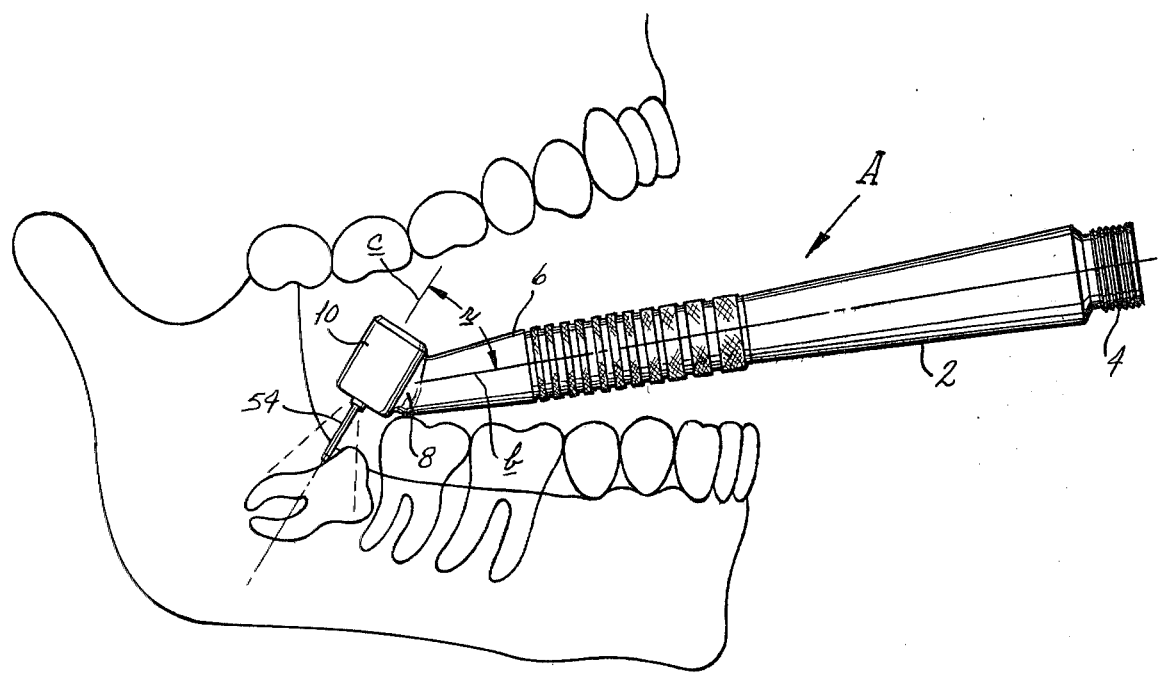
FIG. 3 is a side elevational view of the handpiece showing it being used for surgical removal of an impaction.

Referring now to the drawings, A designates a dental handpiece that is useful for cutting teeth, particularly the teeth at the back of the mouth. It requires a source of compressed air and water for its operation.

The handpiece A includes (FIGS. 1 & 2) a handle 2 having a threaded section 4 at its rear end, and this section is configured to couple with a conventional adapter through which compressed air and water are supplied to the handpiece A. At its forward end, the handle 2 is joined to a shank 6 which tapers downwardly to a connecting portion 8 that merges with a turbine head 10 of generally cylindrical configuration. The handle 2, the shank 6, and the head 10 have longitudinal axes a, b, and c, respectively, which are in the same plane and therefore intersect. The shank 6 forms a continuation of the handle 2, and its axis b may be coaxial with the axis a of the handle (as illustrated) or the axis b may be located at a slight angle with respect to the axis a of the handle 2. The included angle between the axis c of the turbine head 10 and the axis b of the shank 6, measured at the back of the head 10, is, in constrast to conventional handpieces, an acute angle d (FIG. 2) which preferably ranges between 30° and 60°. For surgical impactions, the angle d is preferably about 45°.

Both the handle 2 and the shank 6 are of tubular configuration and their hollow interiors are in communication at the juncture of the handle 2 and shank 6. The turbine head 10 has a bore 12 that is concentric to the head axis c, and this bore is separated from the interior of the shank 6 by a cross wall 14 (FIG. 2) that closes the end of the shank 6. The end of the bore 12 which faces generally forwardly, that is away from the shank 6 and handle 2, is closed by an end wall 16 containing a central aperture 18. At the opposite end of the bore 12, the turbine head 10 is provided with external threads over which an end cap 20 threads to close the back end of the bore 12. This end of the bore 12 contains an indentation 21 (FIG. 1).

The handle 2 is provided with a plug 22 (FIG. 2) that fits tightly into the hollow interior of its threaded end section 4. Extended through the plug 12 as well as through the entire hollow interior of the handle 2 is an air tube 24 which at the juncture of the handle 2 and the shank 6 couples with another air tube 26 that extends all the way to turbine head 10. While the interior of the turbine head 10 is separated from the hollow interior of the shank 6 by the cross wall 14, the air tube 26 opens through the wall 14 at a discharge nozzle 28, which is smaller in diameter than the tube 26 and is offset toward one side of the shank 6. The cross wall 14 also contains a return aperture 30 which is offset toward the other side of the shank 6. The return aperture 30, while being at the same depth in the bore 12 as the discharge nozzle 28, is considerably larger in cross section than the discharge nozzle 28. The aperture 30 merely provides communication between the interior bore 12 of the turbine head 10 and the hollow interior of the shank 6.

Aside from two air tubes 24 and 26, the handle 2 and shank 6, within their hollow interiors, also contain a water tube 32 (FIG. 2) which is considerably smaller in diameter than the air tubes 24 and 26. The rear end of the water tube 32 projects through the plug 22, while the forward end projects through the cross wall 14 and thereafter through end wall 16 of the turbine head 10. The forward end of the water tube 32 terminates shortly beyond the end wall 16 and is oriented at an acute angle with respect to the axis c of the head 10 so that water discharged from the tube 32 is directed toward the axis c. Finally, the plug 22 in the threaded end section 4 of the handle 2 also contains a short vent tube 34 that terminates a short distance into handle 2 so as to vent the interior of the handle 2.

The air tube 24, the water tube 32, and the vent tube 34 are arranged in the plug 22 such that they align with corresponding air, water, and vent lines of an adapter that fits against the threaded end section 4 of the handle 2. Indeed, the tubes 24, 32 and 34 are received in the ends of the corresponding tubes of the adapter such that no leakage will occur at the connections. The adapter further carries a ring that threads over the threaded end section 4 and thereby secures the adapter to the handle 2 of the handpiece A. The adapter is conventional and is located at the end of a combined air and water hose.

The turbine head 10 carries a turbine engine 40 (FIGS. 1 & 2) including a cylindrical case 42 that fits snugly in the bore 12, substantially filling the same. The turbine engine 40 also includes a rotor 44 which revolves in the case 42 on ball bearings that are at each end of the case 42. At its forward end of the rotor 44 has a chuck 46 (FIG. 2) that is slightly smaller than the central aperture 18 in the end wall 16 of the head 10. The case 42, on the other hand, has an inlet port 48 and an exhaust port 50 (FIG. 2) in its cylindrical side wall, and also a detent 52 along the back margin of its side wall.

The turbine engine 40 is installed in the turbine head 10 merely by removing the end cap 20 from the head 10 and inserting the engine 40 into the bore 12 with the chuck 46 presented forwardly. The casing 42 advances easily through the bore 12 until its front wall comes against the end wall 16 of the head 10. However, as the case 42 approaches its fully inserted position, care must be exercised to ensure that the detent 52 on the case 42 aligns with the indent 21 in the head 10 so that the former will be received in the latter. Indeed, if the detent 52 and indent 21 are misaligned, the detent 52 will prevent the engine 40 from reaching its fully inserted position. Thus, the detent 52 locates the case 42 in a predetermined position within the head 10, and in that position the inlet port 48 of the engine 14 aligns with the discharge nozzle 28 in the head 10, while the exhause port 50 aligns with return aperture 30 in the head 10. Also, the common axis of rotation for the rotor 44 and the chuck 46 is coincident with the axis c of the head 10. Finally, the end cap 20 is turned down over the threads at the back end of the head 10 to retain the engine 40 in the head 10. The chuck 46 is configured to grip a dental bur r, and when so held, its axis coincides with the head axis c so that the bur r will revolve about the axis c.

The turbine engine 40 may be provided without the case 42 in an arrangement similar to that of the modified handpiece C (FIGS. 6, 7 & 10).

In operation, pressurized air and water are introduced into the handpiece A at the adapter which connects to the threaded section 4 on the handle 2. The pressurized air flows through the two air tubes 24 and 26 and at the end of the tube 26 in the shank 6 it passes into the discharge nozzle 28 where it acquires a high velocity. The high velocity air issuing from the discharge nozzle 28 passes into the case 42 of the engine 40 at the inlet port 48 therein and impinges against the rotor 44, causing the rotor 44 to revolve at extremely high velocity. The air further passes through the case 42 and is discharged therefrom at the exhaust port 50. The exhausted air passes through the return aperture 30 in cross wall 14 and thence into the hollow interior of the shank 6, from which it passes into the hollow interior of the handle 2. The exhausted air leaves the handpiece A through the vent tube 34 that extends through plug 22 in the handle 2.

The water, on the other hand, passes through the water tube 32 and is discharged from the forward end thereof in a stream that is directed toward bur r.

Since axis of the rotation c for the bur r is located at an oblique angle with respect to the axis b of the shank 6, with that angle being such that the bur r is generally projected away from the forward end of the shank 6, the bur r is at an ideal angle for cutting impacted molars (FIG. 3), particularly third molars which are extremely difficult to work on with conventional handpieces. Indeed, this permits the handpiece A to be manipulated in a normal manner within the patient's mouth without opening the mouth to an uncomfortable position or without approaching the tooth from the side as holds true with conventional handpieces. In short, the handpiece A affords a significant improvement in access and maneuverability insofar as surgical impactions are concerned.

Figure 4:
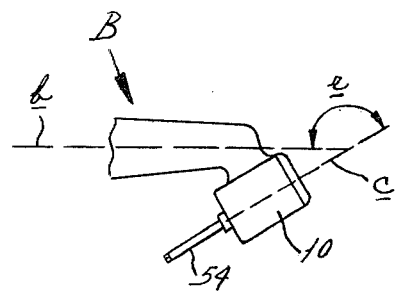
FIG. 4 is a side elevational view of a modified handpiece.

A modified handpiece B (FIG. 4) is quite similar to the handpiece A, but the common axis c of its head 10 and bur r is oriented at an obtuse angle with respect to the axis b of the shank so that bur r projects generally backwardly in the direction of the shank 6. In other words, the included angle d between the axis b and c measured at the back of the head 10 is an obtuse angle. Preferably this angle is between 120° and 160°. The handpiece B is ideally suited for cutting along the back or distal areas of teeth, particularly on those teeth which are set deeply into the mouth such as the molars. With the handpiece B it is no longer necessary to approach decayed areas of most distal teeth from the chewing surfaces, and perhaps remove healthy portions of the teeth to reach the decayed areas, nor is it necessary to stretch the patient's face into contorted and uncomfortable positions.

Another modified handpiece C (FIGS. 5-10) is capable of varying the angle of the axis c about which the bur r revolves. Indeed, the axis c may be positioned at the optimum angle for whatever dental procedure is required. The handpiece C basically includes (FIG. 5) a handle 62, a shank 64 that projects from the forward end of the handle 62, a turbine head 66 at the forward end of the shank 64, and a turbine type dental engine 68 (FIGS. 6 & 7) within the turbine head 66. The dental bur r locks into the engine 68 and is rotated thereby about the axis c of the head 66 and engine 68. The coupling between the shank 67 and the turbine head 66 is such that the former may pivot on the latter about a pivot axis e that is perpendicular to the axis c of rotation for the bur r, and this enables the bur r to be positioned at a wide range of angles with respect to the shank 64.

The handle 62 is of a size that enables it to be easily grasped with the fingers of one hand. It is hollow and slightly tapered, being smaller at its forward end than at its rear end. As its rear end the handle 2 is threaded and otherwise configured to be coupled to a conventional hose adapter through which compressed air and water are supplied to the handpiece C. To this end the large end of the handle 62 receives a plug 72 through which drive air tube 74, a water tube 76, and an air exhaust tube 78 extend. All three tubes are arranged in the plug 72 to align with and fit into corresponding ports in the hose adapter. While the supply tube 74 and water tube 76 extend through the hollow interior of the handle 2 as well as through shank 64, the exhaust tube 78 is only long enough to extend through the plug 72. In this regard, the exhaust air from the engine 68 merely passes through the hollow interior of the handle 2 and leaves through the exhaust tube 78.

The shank 64 is joined firmly to the forward end of the handle 62, but is somewhat smaller in diameter (FIG. 5). Preferably the shank 64 is on the same axis a as the handle 62 so that the shank 64 in effect forms a straight line continuation of the handle 2, although in some instances it may be desirable to have the axis b of the shank 64 at a slight angle with respect to the axis a of the handle 62. The shank 64 for the most part is hollow and the air supply tube 14 and water tube 16 pass into and bifurcate within it.

The forward end of the shank 64 is bifurcated to form a yoke 82 in which the turbine head 66 is received. The yoke 82 includes spaced apart arms 84 and 86 that form a common forwardly presented surface 88 that is concave. Each arm 84 and 86 is also somewhat wedge-shaped in cross-section in that it is wider at its top than at its bottom (FIG. 7), so that the outside surface of each arm 84, 86 tapers inwardly toward the lower margin. The arms 84 and 86 terminate in forwardly, curved or convex end walls 90 (FIGS. 5, 8 & 9) having inwardly directed extensions that provide circular cavities 92 (FIGS. 6 & 7) along the inside faces of the arms 84 and 86. The turbine head 66 is received and retained in the cavities 92, and to permit installation of the head 66 in the yoke 82, the shank 64 and yoke 82 are split at a part line 94 along which a gasket 96 exists (FIG. 6).

Each arm 84 and 86 contains ribs 98 that divide it into three parallel passages—namely, a drive air passage 100, a water passage 102, and an air exhaust passage 104 (FIGS. 7-9). The drive air passages 100 occupy the top or widest portions of their respective arms 84 and 86, while the water passages 102 occupy the lower or narrowest portions. The exhaust passages 104 are between the drive air and water passages 100 and 102. In each arm, 84 and 86, the ribs 98 that separate the passages 100, 102 and 104 curve around parallel to, yet spaced from the end wall 90, and merge together at their curved end portions where they are further joined to the end wall 90 through a blocking web 108 (FIGS. 8 & 9). In the left arm 84 (FIG. 8) this blocking web 108 is offset closer to the narrow lower portion of the arm 24 so that the drive air passage 100 curves around along the end wall 90. In the right arm 86 (FIG. 9) the blocking web 108 is offset toward the wide upper portion of the arm 86 so that the water passage 102 continues around along the curved end wall 86 of that arm.

The initially exposed portions of the passages 100, 102 and 104 in each of the arms 84 and 86 are closed by cover plates 110 and 112, respectively (FIGS. 6-10), that are fastened to their respective arms 84 and 86 parallel to one another and are spaced apart a distance equal to the width of the turbine head 66. Indeed, the plates 110 and 112 fit tightly against the ribs 98 as well as the blocking web 108 to completely enclose the three passages 100, 102, and 104 in the arms 84 and 86 and to isolate them from each other. Both of the plates 110 and 112 have center apertures 114 (FIGS. 8 & 9) which open into the exhaust passages 104 of their respective yoke arms 84 and 86. These apertures 114 are concentric to the pivot axis e for the turbine head 6.

In addition, the plate 110 for the left arm 84 (FIG. 8) contains an arcuate aperture 116 which is concentric to the pivot axis e and overlies the front or curved portion of the drive air passage 100 in that arm. The aperture 116 extends for about 160°. The plate 110 also contains an arcuate groove 118 that overlies the water passage 102 and the exhaust passage 104 and opens toward the other plate 112. Like the aperture 116 the groove 118 is concentric to the axis e and extends for about 160°. The groove 118 communicates with the water passage 102 through a small aperture 120 in the plate 110, that aperture being at the lower end of the groove 118.

The plate 112 that covers the inside face of the right arm 86 has a mirror image arrangement of apertures and grooves (FIG. 9). In particular, it has a center aperture 114 that opens into the end of the exhaust passage 104 and is concentric to the pivot axis e. It also has an arcuate aperture 122 that lies immediately ahead of the center aperture 114 and overlies the curved forward end of the water passage 102 in the arm 86. The aperture 122 is, of course, concentric to the pivot axis e. The plate 112 further contains an arcuate groove 124 that is concentric to the pivot axis e and overlies the end of the drive air passage 100 and the exhaust passage 104 for the arm 86 as well. At that end of the groove 124 which is over the drive air passage 100, the plate 112 is provided with a circular aperture 126 that provides communication between the groove 124 and the air passage 100 in the arm 86.

Overlying each of the plates 110 and 112 is a flat gasket 128 which contains apertures in the identical patterns and shapes as the underlying plate 110 or 112. The gaskets 128 adhere to their respective plates 110 and 112 and may be formed from a material sold under the trademark TEFLON.

The turbine head 66 possesses a generally spherical configuration and fits into the space between the two arms 84 and 86 of the yoke 82 (FIGS. 6 & 7) where it is retained in place. Indeed, the head 66 has truncated conical projections 130 which extend laterally from it and are snugly received in the circular cavities 92 along the yoke arms 84 and 86, the axis of the projections 130 being coincident to the pivot axis e for the head 66. In effect, the projections 130 constitute trunnions which rotate in the circular cavities 92 and enable the head 66 to pivot with respect of the yoke 82 about the pivot axis e. In this regard, the back face of the head 66 is contoured such that it conforms to the concave forward surface 88 on the yoke arms 84 and 86.

The head 66 actually consists of two halves which fit together and abut along a part line 131 that bisects the two projections 130. Here the halves are provided with machined faces to assure snug contact. The head 66, when its two halves are joined together, possesses a spheroidal configuration and contains a cylindrical cavity 132 (FIGS. 6 & 7) in which the turbine engine 68 is housed. In addition, the head 66 contains two exhaust ports 136 which are centered with respect to the projections 130 (FIG. 10) and align with the circular center apertures 114 in the plates 110 and 112 that line the insides of the arms 84 and 86. To the sides of its exhaust port 136, each projection 130 further has a drive air port 138 (FIGS. 6 & 10) and a water port 140. The drive air port 138 for the one projection 130 that is against the left plate 110 aligns with the arcuate aperture 116 in that plate 110, while the drive air port 138 in the other projection 130 that is against the right plate 112 aligns with the arcuate groove 124 in that plate 112. Moreover, the two drive air ports 138 lead toward and open into the cylindrical cavity 132 at 180° from each other, each being set at somewhat of an angle so that the air flows generally tangentially with respect to the cavity 132. Similarly, the water port 140 in the projection 130 that is against the left plate 110 aligns with arcuate groove 118 in that plate 110, while the water port 140 in the other projection 130 that is against the right plate 112 aligns with the arcuate aperture 122 in that plate 112. The exhaust ports 136, the drive air port 138 and the water ports 140 are all isolated from each other at the ends of the projections 130 by the gaskets 128.

Each water port 140 connects with a water passage 142 to lead to a separate nozzle 144 (FIG. 5) in the end of the head 66, those nozzles being directed at the axis of rotation c where the tip of the bur r rotates.

The turbine engine 68 is housed within the cylindrical cavity 132 of the turbine head 66 (FIGS. 6 & 7) and includes a rotor 154 (FIG. 6) which revolves within the cavity 132 about an axis rotation c and has cup-like turbine vanes or blades 155 on it and a chuck 156 (FIG. 7) that receives and holds the dental bur r. Unlike conventional turbine engines, the engine 68 is driven by a pair of air streams which discharge into it through the drive air ports 138 that are located 180° apart in the turbine head 66.

Finally, the yoke 82 is fitted with a detent mechanism 162 (FIG. 10) that includes a spring-loaded pin 164 which aligns with apertures 166 arranged in a row on the turbine head 66. The pin 164 is retractable away from the head 66, and when so retracted, it permits the head 66 to rotate about the pivot axis e so that the head 66 can be positioned at any desired angle with respect to the yoke 22. However, when the pin 164 is released, its spring urges it inwardly into the nearest aperture 166, and therefore the pin 164 holds the head 66 in a fixed position.

In operation, the user selects a dental bur r appropriate for the dental procedure which is to be performed. Also, the threaded end of the handle 62 is coupled by means of an adapter to a hose that supplies both high pressure air and water to the handpiece C, the former being introduced into the drive air tube 74 and the latter into the water tube 76. The hose also contains an exhaust line which withdraws air from the exhaust tube 78. The high pressure air passes through the drive air tube 74 and into the drive air passages 100 in the two arms 84 and 86 of the yoke 82. It leaves the left arm 84 through the arcuate aperture 116 in the plate 110 of that arm and enters the aligned drive air port 138 of the turbine head 66, whereupon the air flows into the turbine engine 68 and impinges against the vanes or blades 155 of its rotor 154, thereby causing the rotor 154 to revolve at an extremely high velocity. The air flows around the rotor 154 for slightly less than 180° and leaves the rotor 154 at the exhaust port 136 in the opposite projection 130. The low pressure exhausted air then flows through the center aperture 114 in the right plate 112 that covers the yoke arm 86 and thence through the exhaust passage 104 in that arm. This passage communicates with the interior of the shank 4 and handle 2 to which the exhaust air passes.

More of the high pressure air flows through the drive air passage 100 in the right arm 86, and this air enters the turbine head 66 through the circular aperture 126 and arcuate groove 124 in the plate 112 that overlies that arm, since the groove 124 aligns with the drive air port 138 in the projection 130 that is against the plate 112. This air likewise impinges against the blades 155 of the rotor 154 and flows around the rotor 154 for less than 180°, whereupon it is discharged through the exhaust port 136 in the projection 130 that is against the left plate 110, flowing therefrom into the left arm 84 through the aligned exhaust port 134 and center aperture 114. This low pressure air likewise finds its way into the interior of the handle 62.

Since the drive air is delivered to the turbine engine 68 at two locations opposite the rotor 154, the rotor 154 develops considerably more torque than the rotors of conventional turbine engines. Indeed, it is estimated that the torque is increased by at least 35% with no adverse affect on speed.

The water flows through the water tube 76 to the water passages 102 in the two arms 84 and 80. Insofar as the left arm 84 is concerned, the water passes through the small aperture 120 in the plate 110 and into the arcuate groove 118, and since the water port 140 in the adjacent projection 130 of the turbine head 66 aligns with that groove, the water passes into that port 140 and thereupon flows through the passage 142 in the turbine head 66 to the nozzle 144, from which it is discharged toward the rapidly rotating bur r. Similarly, more water flows through the water passage 102 in the right arm 86, and this water leaves the arm 86 through the arcuate aperture 122 which aligns with the water port 140 in the projection 130 that is against the plate 112. Thereupon the water flows through the other water passage 142 to the other nozzle 144 in the turbine head 66, being discharged therefrom against the revolving bur r. Thus, the bur r is supplied with water from two directions, so if one of the water sprays is in some way obstructed, the rotating bur r is nevertheless washed by the other spray.

Figure 11:
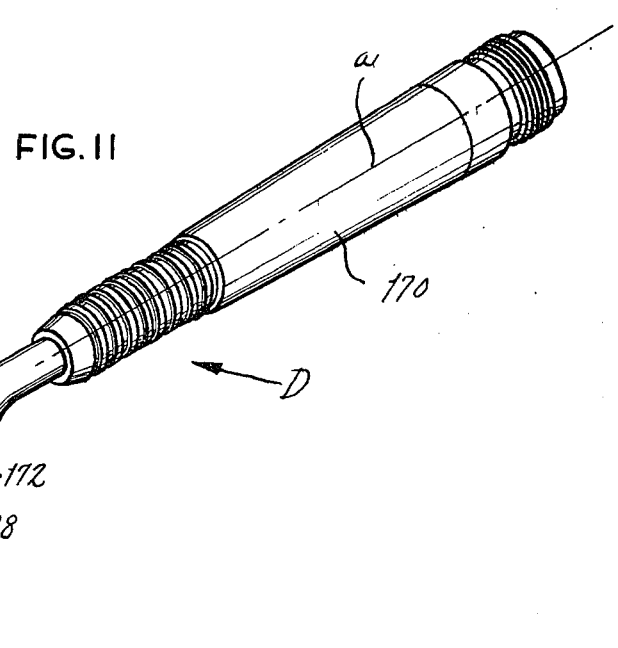
FIG. 11 is a perspective view of still another modified handpiece having a turbine head that pivots.
Figure 12:
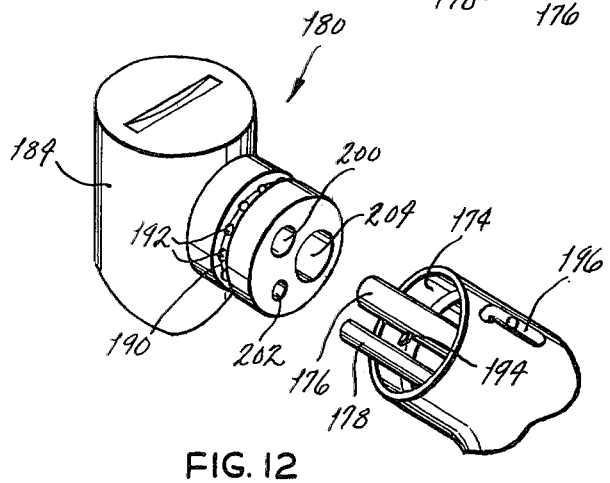
FIG. 12 is an exploded view showing the region at which the head and shank for the handpiece of FIG. 11 are joined together.

Still another modified handpiece D (FIGS. 11–13) provides about the same versatility as the handpiece C in a somewhat simpler configuration, but it does not provide the high torque of the handpiece C. The handpiece D includes a handle 170 (FIG. 11) which is identical to the handle 2 of the handpiece A and a shank 172 which connects with the small diameter end of the handle 170 and curves away from the axis a of the handle 170 so that the forward end of the shank 172 is somewhat offset. At its forward end, the shank 172 is provided with a circular socket 174 (FIGS. 12 & 13) that opens toward the extended axis a of the handle 172 and indeed the axis f of the socket 174 is perpendicular to the axis a. Both the handle 170 and the shank 172 contain a drive air tube 176 and a water tube 178 that terminate in the region of the socket 174 (FIG. 11). Both tubes 176 and 178 are flexible.

In addition to the handle 170 and the shank 172, the handpiece D further includes a turbine head 180 (FIG. 11) as well as a conventional dental engine 182 that holds a bur r and rotates it about the axis c of the engine 182. The head 180 includes an enlarged cylindrical portion 184 having a cylindrical cavity into which the dental engine 182 fits. In addition, the head 180 has a projection 188 (FIGS. 12 & 13) that extends laterally from the head 180, with the end of the projection 188 being received in the socket 174 of the shank 172. This enables the head 180 to pivot about the axis f of the socket 174. In this regard, the projection 188 contains an annular groove 190 which is concentric to and opens outwardly away from the pivot axis f and a plurality of equally spaced holes 192 that open out of the groove 190. The forward end of the shank 172, on the other hand, contains a fixed lug 194 which projects into the groove 190 and also a retractable lug 196 which is located 180° from the fixed lug 194 and likewise projects into the groove 190 in the region of the holes 192. Indeed the end of the lug 196 is designed to fit into a hole 192 and thereby prevent the head 180 from rotating on the shank 172. The retractable lug 196 is actuated from the exterior surface of the shank 172 such that it can be withdrawn from any particular hole 192, but not from the groove 190. Thus, the retractable lug 196 and the fixed lug 194 serve to retain the turbine head 180 engaged with the socket 174 of the shank 172. The retractable lug 196 further prevents the head 180 from pivoting when it is in one of the holes 192.

Figure 13:
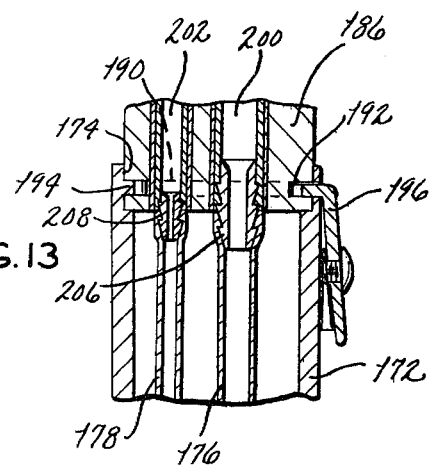
FIG. 13 is a sectional view taken along line 13—13 of FIG. 11.

The projection 188 on the head 180 contains (FIG. 12) a drive air port 200, a water port 202, and an exhaust port 204. The drive air port 200 is connected by means of a short connecting sleeve 206 with the flexible drive air tube 176 in the handle 170 and shank 172 (FIG. 13). At its opposite end it opens into the inlet port to the turbine engine 182 so that the high pressure drive air which is supplied through it rotates the rotor of the turbine engine 182. The exhaust port 204 aligns with the exhaust port of the engine and at its opposite end opens into the hollow interior of the shank 172, so that the spent air is permitted to escape through the shank 172 and handle 170. The water tube 178 connects by means of a short connecting sleeve 208 with the water port 202 within the head 180 (FIG. 13), and this port leads to a nozzle 210 (FIG. 11) which is directed to the tip of the bur r that is carried by the rotor of the engine 182.

In use, the dentist selects the desired bur r and then installs it in the rotor of the turbine engine 182. Thereupon, he withdraws the retractable lug 196 sufficiently to bring it out of the hole 192 in the projection 188 on the turbine head 180, and rotates the turbine head 180 to change the orientation of the bur r so that it assumes a position which is suitable for the particular dental procedure he desires to perform. When the turbine head 180 is in the desired position, the retractable lug 196 is released, allowing it to drop into the closest hole 192 in the projection 188 on the turbine head 180. This locks the turbine head 180 against rotation. Thereupon, the compressed air and water are supplied to the handpiece D. The air flows through the drive air tube 176 to the drive air port 200 in the head 180, from which it passes into the turbine engine 182, causing the rotor of the engine 182 to revolve at extremely high velocity. The air leaves the rotor through the exhaust port 204 and flows through the shank 172 and handle 170.

This invention is intended to cover all changes and modifications of the example of the invention herein chosen for purposes of the disclosure which do not constitute departures from the spirit and scope of the invention.

What is claimed is:

1. A dental handpiece comprising: a handle having forward and rear ends, a shank projection from the forward end of the handle, the shank being bifurcated so as to have two spaced apart arms; a turbine head between the arms of the bifurcated shank; a turbine-type dental engine in the turbine head for rotating a dental bur about an axis, the turbine head being attached to the arms of the shank such that the position of the engine axis can be varied with respect to the handle; and means extended through the handle and through both arms of the shank for supplying high pressure air to the turbine engine to rotate the dental bur.

2. A dental handpiece according to claim 1 wherein the turbine head has a nozzle directed toward the bur when it is coupled to the turbine engine, and further comprising means extended through the handle and shank for delivering water to the bur.

3. A dental handpiece according to claim 1 and further comprising means for locking the turbine head in a fixed position with respect to the shank.

4. A dental handpiece according to claim 1 wherein the turbine head has two ports through which air from the arms on the shank is directed into the turbine engine, with the ports being circumferentially spaced from each other around the periphery of the engine.

5. A dental handpiece according to claim 4 wherein the turbine head contains two exhaust ports for receiving air that passes through the turbine engine, with one exhaust port opening into the one arm of the shank and the other exhaust port opening into the other arm of the shank.

6. A dental handpiece according to claim 5 wherein the head pivots about an axis that is fixed with respect to the shank, and the exhaust ports are concentric with respect to the pivot axis.

7. A dental handpiece according to claim 5 and further comprising means extended through the handle and shank for delivering water through both arms of the shank to the turbine head, and wherein the turbine has a water port located opposite each of arms for receiving water from the arms and water nozzles directed toward axis of rotation for the engine, each nozzle being in communication with a different water port in the head.

8. A dental handpiece according to claim 1 wherein the arms of the shank have pockets which open toward each other, and the turbine head has projections which extend into the pockets, whereby the turbine head is retained on the shank.

9. A dental handpiece according to claim 1 wherein the turbine head is connected to the shank only at one side of the turbine head, and the high pressure air enters the turbine head in the region of the connection between the shank and turbine head.

10. A dental handpiece comprising: a handle having forward and rear ends; a shank at the forward end of the handle, the shank being bifurcated such that it has two arms; a turbine head mounted on the shank between the two arms of the shank; a turbine-type dental engine within the head and being capable of holding and rotating a dental bur; and means within both arms of the shank and within the head for introducing pressurized air to the engine at two locations around the axis of rotation for the engine, whereby the engine develops high torque.

11. A dental handpiece comprising: a handle; a shank projected from the forward end of the handle, the shank being bifurcated so as to have two spaced apart arms, one of the arms containing a drive air passage and the other of the arms containing an exhaust air passage; a turbine head mounted between the two arms of the shank such that it can swivel about a first axis that is transverse to the shank and passes through the two arms, the head having a drive air port which aligns with the drive air passage of the one shank arm in various positions of the rotation for the head, the head further having an exhaust air port which aligns with the exhaust air passage of the other shank arm in various positions of rotation for the head; a turbine-type dental engine located within the turbine head such that it is adapted to receive high pressure drive air from the drive port and to exhaust lower pressure exhaust air into the exhaust port; and means within the shank and handle for supplying high pressure air to the drive air passage of the one shank arm.

12. A dental handpiece according to claim 11 wherein at least one of the ports is circular and concentric to the first axis about which the turbine head swivels.

13. A dental handpiece according to claim 11 wherein each of the shank arms has a drive air passage and an exhaust air passage and the turbine head has a drive air port and an exhaust air port on each side of the turbine-type dental engine, with the drive air port and the exhaust air port on the one side of the engine aligning with the drive air passage and the exhaust air passage, respectively, in the one shank arm, and the drive air port and the exhaust air port on the other side of the engine aligning with the drive air passage and the exhaust air passage, respectively, in the other shank arm.

14. A dental handpiece according to claim 11 wherein at least one of the shank arms contains a water passage and the turbine head has a water port and a nozzle, the port at one end aligning with the water passage in various positions of the head and at its other end being connected with the nozzle, the nozzle being directed at the location for the dental bur.

* * * * *